US010391003B2

(12) United States Patent
Yamada

(10) Patent No.: US 10,391,003 B2
(45) Date of Patent: Aug. 27, 2019

(54) DISPOSABLE ARTICLE, AND METHOD FOR PRODUCING AND METHOD FOR SELLING THE SAME

(71) Applicant: Kikuo Yamada, Shinagawa-ku (JP)

(72) Inventor: Kikuo Yamada, Shinagawa-ku (JP)

( * ) Notice: Subject to any disclaimer, the term of this patent is extended or adjusted under 35 U.S.C. 154(b) by 0 days.

(21) Appl. No.: 15/780,882

(22) PCT Filed: Jun. 1, 2016

(86) PCT No.: PCT/JP2016/066156
§ 371 (c)(1),
(2) Date: Jun. 1, 2018

(87) PCT Pub. No.: WO2017/094275
PCT Pub. Date: Jun. 8, 2017

(65) Prior Publication Data
US 2018/0280208 A1 Oct. 4, 2018

Related U.S. Application Data

(60) Provisional application No. 62/263,088, filed on Dec. 4, 2015.

(30) Foreign Application Priority Data

Dec. 11, 2015 (JP) ................. 2015-242216

(51) Int. Cl.
A61F 13/15 (2006.01)
A61F 13/49 (2006.01)
A61F 13/511 (2006.01)
A61F 13/496 (2006.01)
A61F 13/513 (2006.01)
B32B 5/02 (2006.01)
B32B 7/12 (2006.01)
B32B 25/08 (2006.01)
B32B 25/10 (2006.01)
A61F 13/53 (2006.01)
A61F 13/539 (2006.01)
A61F 13/84 (2006.01)

(52) U.S. Cl.
CPC ........ *A61F 13/49012* (2013.01); *A61F 13/15* (2013.01); *A61F 13/15585* (2013.01); *A61F 13/496* (2013.01); *A61F 13/511* (2013.01); *A61F 13/513* (2013.01); *B32B 5/022* (2013.01); *B32B 7/12* (2013.01); *B32B 25/08* (2013.01); *B32B 25/10* (2013.01); *A61F 2013/1556* (2013.01); *A61F 2013/530007* (2013.01); *A61F 2013/53908* (2013.01); *A61F 2013/8408* (2013.01); *A61F 2013/8488* (2013.01); *B32B 2262/0253* (2013.01); *B32B 2307/718* (2013.01); *B32B 2307/724* (2013.01); *B32B 2307/728* (2013.01); *B32B 2555/02* (2013.01)

(58) Field of Classification Search
CPC ............... A61F 13/49012; A61F 13/15; A61F 13/15585; A61F 13/496; A61F 13/511; A61F 13/513; B32B 5/022; B32B 7/12; B32B 25/08; B32B 25/10
USPC ..................................................... 428/537.5
See application file for complete search history.

(56) References Cited

U.S. PATENT DOCUMENTS 6,648,869 B1 * 11/2003 Gillies .............. A61F 13/51104
604/385.101
2003/0125697 A1 7/2003 Bushman et al.
2012/0311770 A1 * 12/2012 Nakajima ......... A61F 13/49011
2/401

FOREIGN PATENT DOCUMENTS

| EP | 2 011 464 A1 | 1/2009 |
|---|---|---|
| EP | 3 115 196 A1 | 1/2017 |
| EP | 3 231 302 A1 | 10/2017 |
| JP | 2001-507595 | * 6/2001 |
| JP | 2001-507595 A | 6/2001 |
| JP | 2005-342531 | * 12/2005 |
| JP | 2005-342531 A | 12/2005 |
| JP | 2011-167412 | * 9/2011 |
| JP | 2011-167412 A | 9/2011 |

OTHER PUBLICATIONS

International Search Report dated Aug. 16, 2016 in PCT/JP2016/066156, filed on Jun. 1, 2016.
Extended European Search Report dated May 7, 2019, in European Patent Application No. 16870216.5 (10 pages).

* cited by examiner

*Primary Examiner* — Leszek B Kiliman
(74) *Attorney, Agent, or Firm* — Oblon, McClelland, Maier & Neustadt, L.L.P.

(57) ABSTRACT

To provide a user-friendly disposable article including a disposable base fabric provided with at least one of a permeable sheet and a fiber sheet, and multiple elastic members that are joined to at least one of the permeable sheet and the fiber sheet so as to have a joined part and a non-joined part; and a joining part for joining the disposable base fabric and an article to be attached so that the multiple elastic members give an elastic force to a surface to be applied to the skin, arranging the disposable base fabric on the surface side for applying to the skin.

9 Claims, 17 Drawing Sheets

Z DIRECTION

ND METHOD FOR
DISPOSABLE ARTICLE, AND METHOD FOR PRODUCING AND METHOD FOR SELLING THE SAME

TECHNICAL FIELD

The present invention relates to a disposable article such as disposable underwear and a disposable diaper, a method for producing the disposable article, and a method for selling the disposable article.

BACKGROUND ART

Conventionally, various proposals have been made on a disposable textile product, and it has been proposed to intermittently bond multiple elastic members between two sheet materials to form shirring parts using the elastic members, and to adopt the shirring parts, for example, around a waist part or girth part of a disposable diaper.

CITATION LIST

Patent Literature

Patent Literature 1: JP 2005-80859 A

SUMMARY OF THE INVENTION

Problems to be Solved by the Invention

However, the use of shirring parts is limited to obtain the feel and the beauty of appearance, for example, there has not been a sufficient proposal for a stuffiness measure of an absorbent body into which a liquid such as urine and sweat is absorbed in a disposable diaper.

Accordingly, an object of the present invention is to provide a user-friendly disposable article.

Further, an object of the present invention is to realize a method for producing a user-friendly disposable article.

Furthermore, an object of the present invention is to realize a method for selling a disposable article with large user benefits.

Means for Solving the Problems

The disposable article according to Claim 1 of the present invention including: a disposable base fabric having at least one of a permeable sheet and a fiber sheet, and a plurality of elastic members to be joined; and a joining part for joining the disposable base fabric and an article to be attached so that the plurality of elastic members give an elastic force to a surface to be applied to the skin, arranging the disposable base fabric on the surface side for applying to the skin.

The disposable article according Claim 6 of the present invention including: a disposable base fabric having a permeable sheet, and an elastic member arranged at least in the vicinity of the center of the permeable sheet; and a joining part for joining an article to be attached and the disposable base fabric, arranging the disposable base fabric on the surface side for applying to the skin.

The method for producing a disposable article according to Claim 15 of the present invention including: a step of setting a disposable base fabric having a permeable sheet, and a plurality of elastic members arranged at least in the vicinity of the center of the permeable sheet; and a step of joining an article to be attached and the disposable base fabric, arranging the disposable base fabric on the surface side for applying to the skin.

The method for selling a disposable article according to Claim 18 of the present invention, in which a disposable base fabric having a permeable sheet and a plurality of elastic members arranged at least in the vicinity of the center of the permeable sheet, and an article to be attached are sold as a set.

Advantageous Effect of the Invention

According to the invention according to Claim 1 or Claim 6 of the present invention, a user-friendly disposable article can be realized.

According to the invention according to Claim 15 of the present invention, a method for producing a user-friendly disposable article can be realized.

According to the invention according to Claim 18 of the present invention, a method for selling a disposable article with large user benefits can be realized.

MODE FOR CARRYING OUT THE INVENTION

Figure 1:
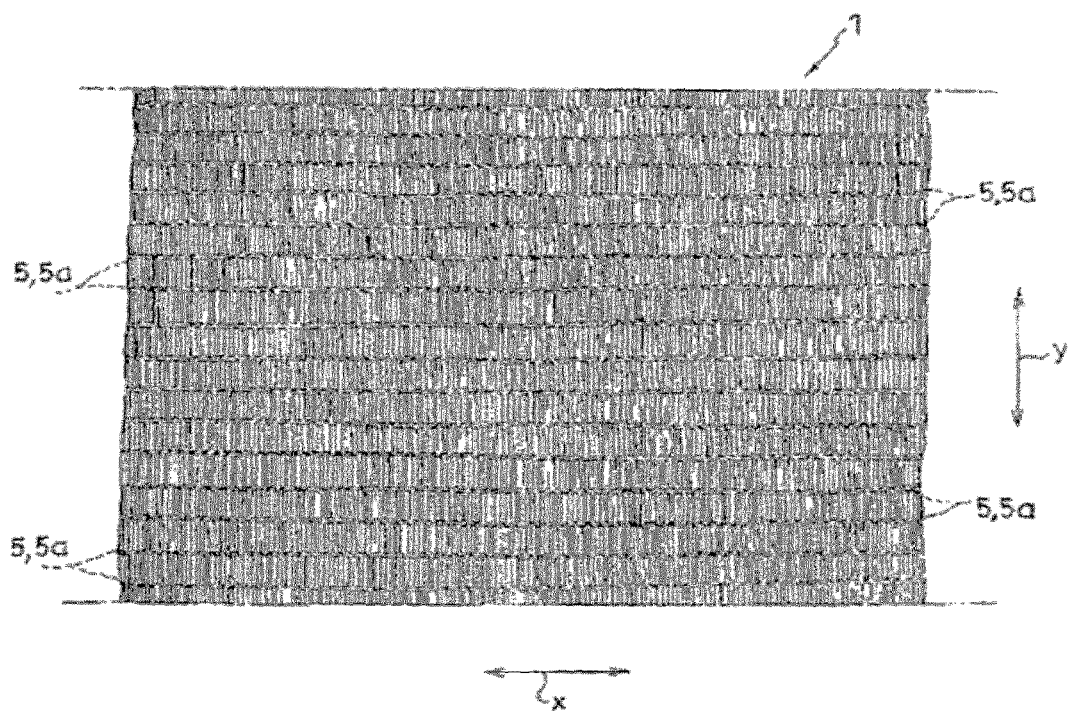
FIG. 1 is a diagram showing a base fabric 1 for a disposable textile product of the present embodiment.
Figure 2:
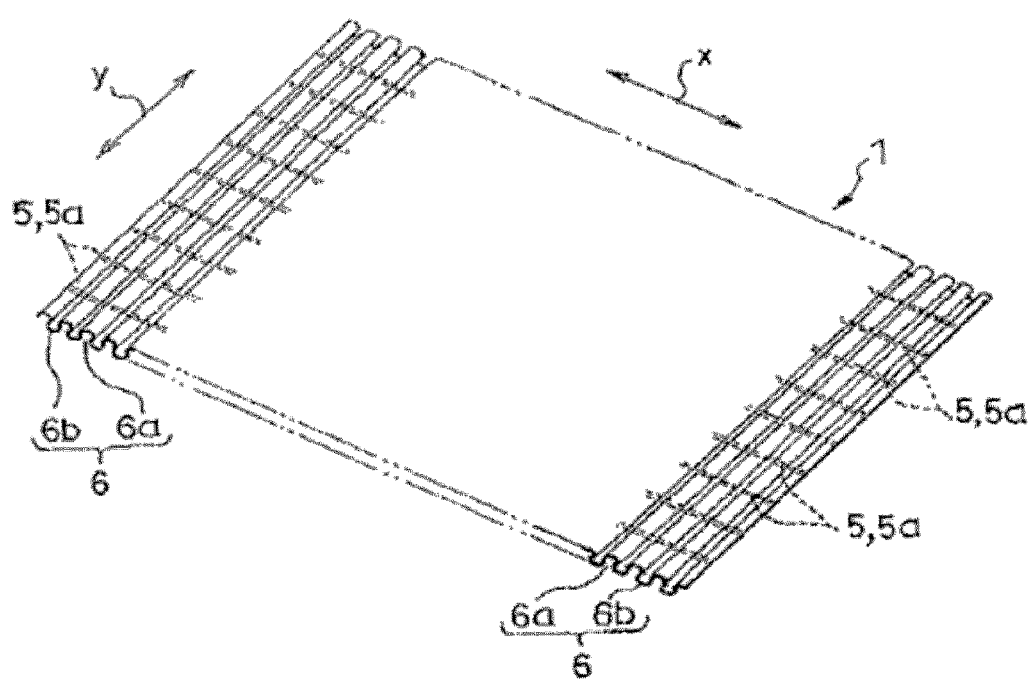
FIG. 2 is a perspective view of a base fabric 1 for a disposable textile product of FIG. 1.

Hereinafter, the embodiments of the present invention will be described with reference to the drawings. In FIG. 1, a surface state of a base fabric 1 of the present embodiment is shown. In the present embodiment, a base fabric 1 is used as a surface material 15 of an absorbent body 14 of a disposable textile product, as described later (see FIG. 8). In FIG. 1, a base fabric 1 is continuous in the x direction that is a first direction. The reference number 5 denotes elastic members arranged inside the base fabric, and the diagram shows an aspect in which a large number of uneven surfaces are formed by a large number of elastic members 5. As shown in FIG. 2, a large number of shirring parts 6 are repeatedly formed along the Y direction by a large number of the uneven surfaces. In this regard, as is apparent from the FIGS. 1 and 2, the elastic members 5 are arranged along the X direction and apply an elastic force in the X direction to the base fabric 1. The multiple elastic members 5 described above are arranged at predetermined intervals in the Y direction. In addition, in a case of using an elastic member in a lattice shape, a large number of the shirring parts 6 that have been described above can be formed by one elastic member in a lattice shape. Further, a stretchable film may be used as the elastic member in place of a large number of the elastic members 5. As the stretchable film, a stretchable elastic film such as a urethane film, a silicon film, or an elastomer film can be used.

Figure 4:
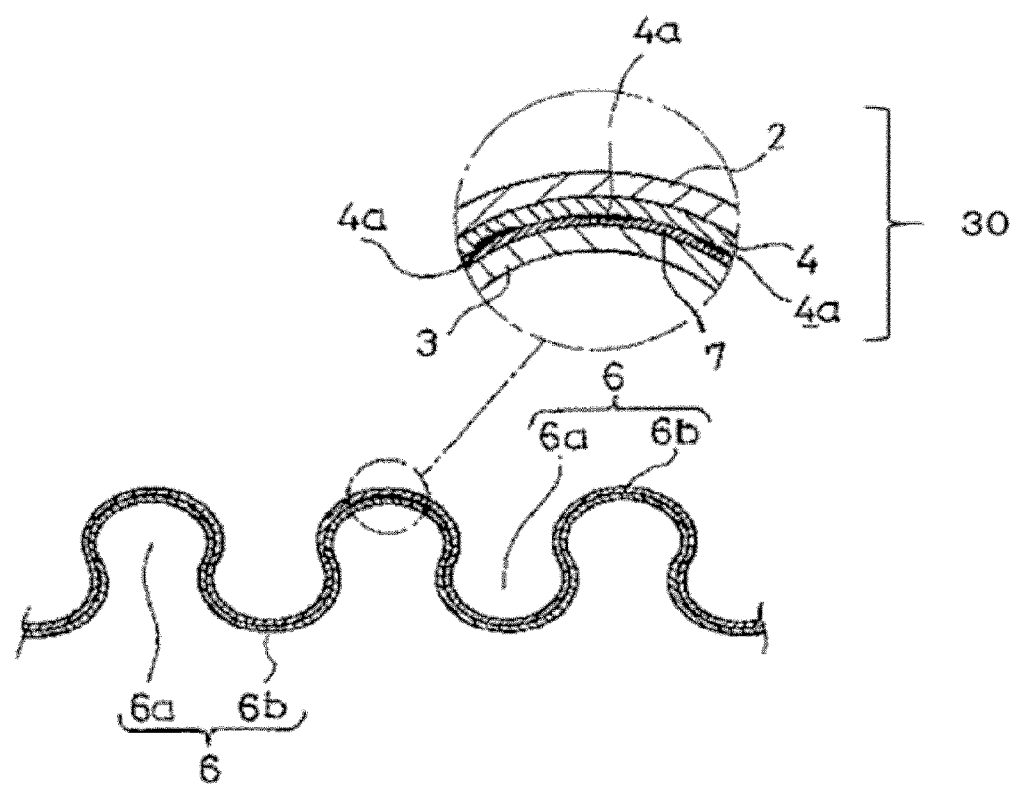
FIG. 4 is a sectional view along the line A-A of FIG. 3.
Figure 5:
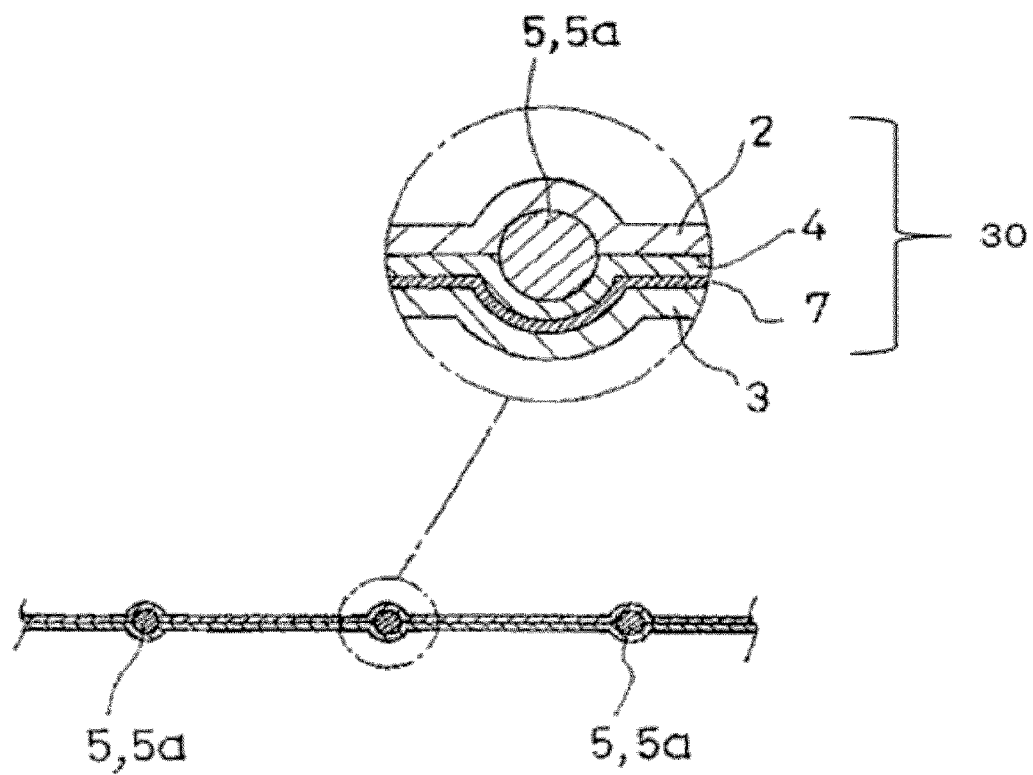
FIG. 5 is a sectional view along the line B-B of FIG. 3.

As shown in FIGS. 4 and 5, a base fabric 1 has a first fibrous sheet 2 that is a sheet having permeability, a second fibrous sheet 3 that is a sheet having permeability similarly, and a fiber material 4 having liquid diffusibility, which is interposed between the first fibrous sheet 2 and the second fibrous sheet 3, and is constituted of a laminated sheet 30 formed by laminating the first fibrous sheet 2, the second fibrous sheet 3, and the fiber material 4. The first fibrous sheet 2 and the second fibrous sheet 3 constitute a fiber layer having permeability, and the fiber material 4 is a sheet constituting a fiber layer that has liquid diffusibility. As described above, the laminated sheet 30 is constituted of three layers. Note that in the present embodiment, as described later, the second fibrous sheet 3 is on the side in contact with the skin of a user, and the first fibrous sheet 2 is on the side in contact with an absorbent body 14. Accordingly, a three-layer structure may be formed using a fiber material 4 in place of the first fibrous sheet 2, or a two-layer structure obtained by omitting the first fibrous sheet 2 may be used. Further, the fiber material 4 is omitted, and a two-layer structure including the first fibrous sheet 2 and the second fibrous sheet 3 may also be used. In the present embodiment, since a base fabric 1 is used as a surface material 15 of an absorbent body 14, a hydrophilic fibrous sheet is desirably used as the first fibrous sheet 2 and the second fibrous sheet 3. In the following description, the description will be continued on the assumption that a three-layered structure using the first fibrous sheet 2 is used.

The first fibrous sheet 2 and the fiber material 4 are intermittently joined to each other with elastic members 5 therebetween. It is preferred that the second fibrous sheet 3 and the fiber material 4 are also intermittently joined to each other. In the present embodiment, the description will be continued on the assumption that the second fibrous sheet 3 and the fiber material 4 are intermittently joined and integrated to each other so as to form a part where the second fibrous sheet 3 and the fiber material 4 are joined to each other and a part where the second fibrous sheet 3 and the fiber material 4 are not joined to each other, and then elastic members 5 and the first fibrous sheet 2 are joined to the integrated second fibrous sheet 3 and fiber material 4.

As the joining method, for example, adhesion joining, thermal fusion joining, or ultrasonic joining is used, and adhesion joining is preferred from the viewpoint of the ease of work. Hereinafter, embodiments in a case where adhesion joining is adopted as a joining method will be described.

Figure 6:
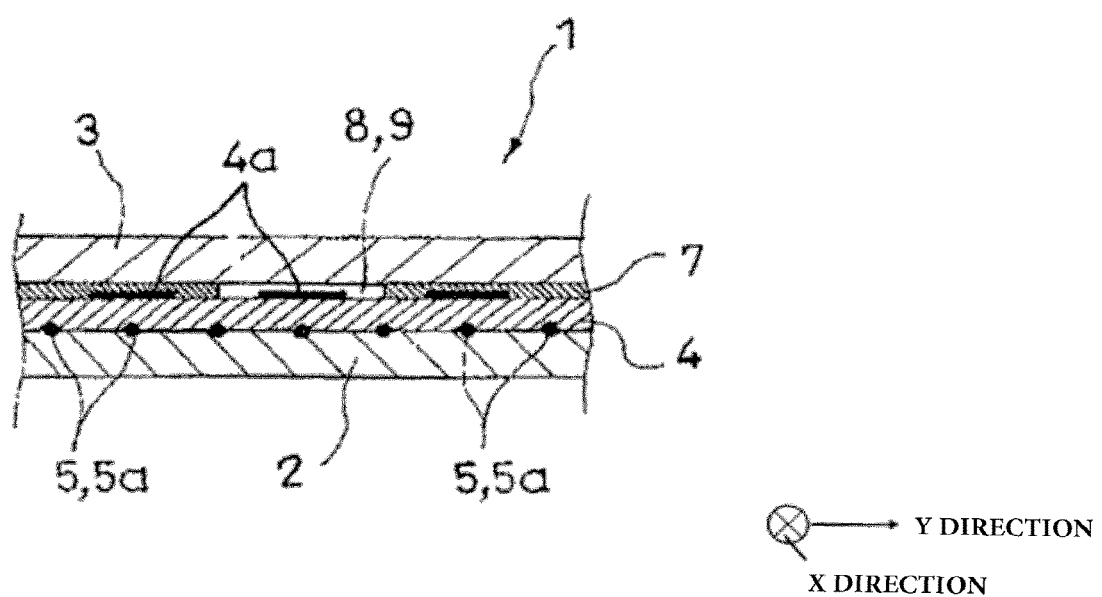
FIG. 6 is a diagram showing a laminated sheet of a base fabric 1.
Figure 7:
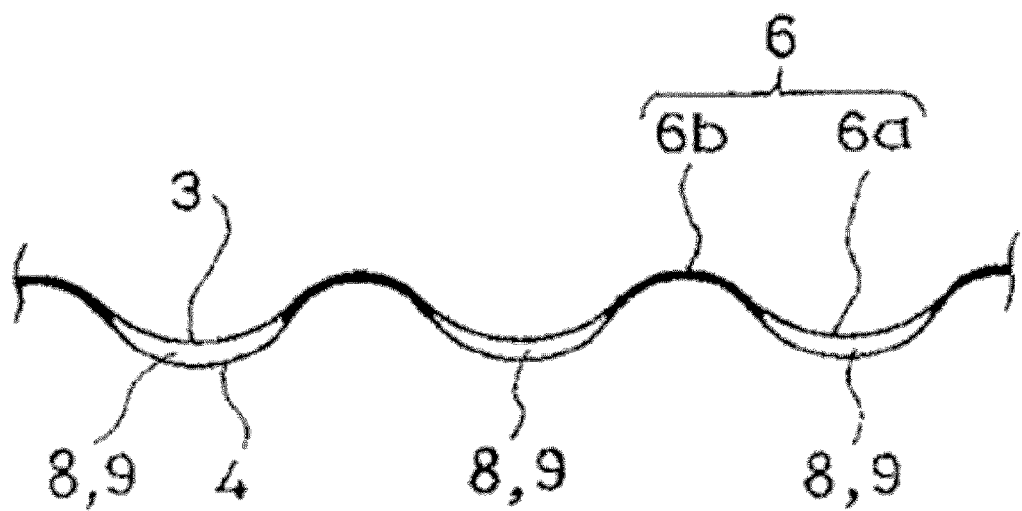
FIG. 7 is a diagram showing spaces 9 formed between a second fiber sheet 3 and a fiber material 4.

In the adhesion joining as the joining method, a hot-melt adhesive is preferably used as an adhesive agent. Hereinafter, an embodiment in a case where a hot-melt adhesive is used as an adhesive agent will be described. In order to intermittently join a second fibrous sheet 3 and a fiber material 4 using a hot-melt adhesive, as shown in FIG. 6, the hot-melt adhesive is intermittently applied to the fiber material 4 (alternatively, the hot-melt adhesive may be intermittently applied to the second fibrous sheet 3), and both are laminated, and integrally joined. At this time, a non-adhesive part 8 in which an adhesive layer 7 does not exist is formed between the second fibrous sheet 3 and the fiber material 4, and a space 9 is formed by the non-adhesive part 8. In addition, since elastic members 5 are interposed between the first fibrous sheet 2 and the fiber material 4, by joining the first fibrous sheet 2 and the fiber material 4 to each other at a position of each of the elastic members 5, the first fibrous sheet 2 and the fiber material 4 are intermittently joined to each other. That is, a hot-melt adhesive is sprayed and applied onto the peripheral surfaces of a large number of elastic members 5 arranged in parallel rows at predetermined intervals as shown in FIG. 6, the elastic members 5 applied with the hot-melt adhesive are positioned between the surface of the fiber material 4 in a laminated sheet of the second fibrous sheet 3 and the fiber material 4 and the first fibrous sheet 2, and the elastic members 5 are sandwiched between the surface of the fiber material 4 in the laminated sheet and the first fibrous sheet 2, laminated, and integrally joined. Although not particularly shown in FIG. 6, an opposing surface of the first fibrous sheet 2 and the fiber material 4 having no elastic member 5 is a non-adhesive part 8, and a space 9 is formed by the non-adhesive part 8. In FIG. 7, an aspect in which spaces 9 are formed by the non-adhesive parts 8 in shirring parts 6 is shown. In this way, due to the structure in which a space 9 is formed by a non-adhesive part 8, each function of the moisture transpiration ability, the heat dissipation, and the moisture permeability in a base fabric 1 is improved.

Figure 3:
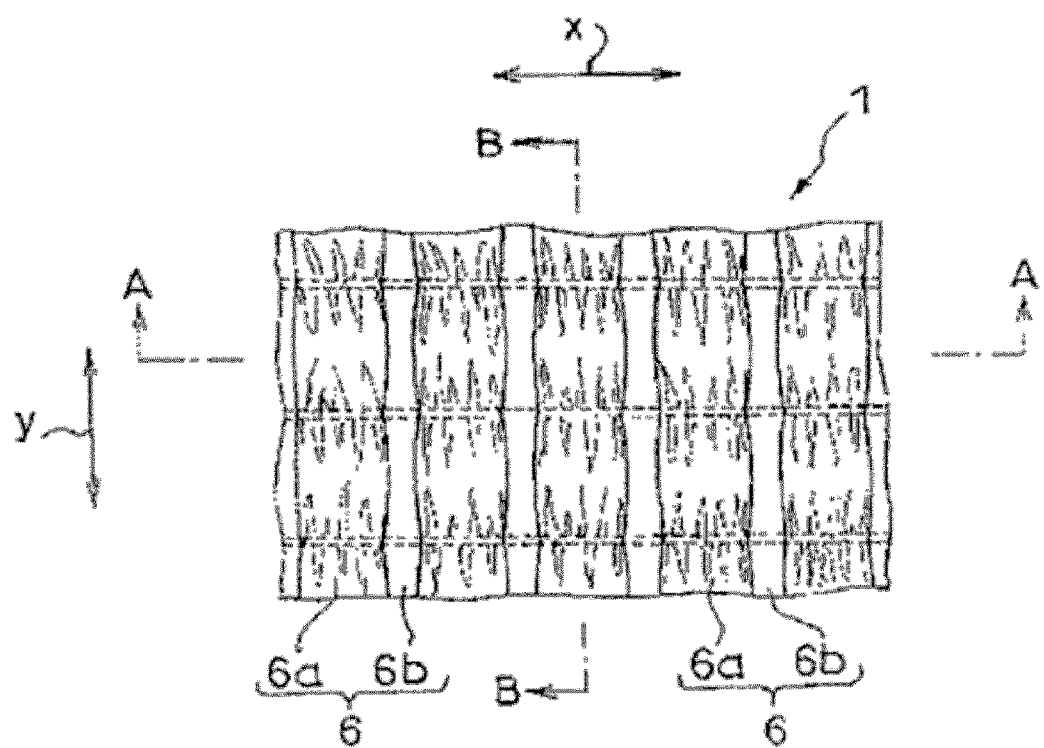
FIG. 3 is an enlarged view of abase fabric 1 for a disposable textile product of FIG. 1.

As shown in FIGS. 2, 3, and 4, by forming protrusion parts 6a and concave parts 6b continuously, a large number of shirring parts 6 are formed.

As a method for forming the shirring parts 6 including protrusion parts 6a and concave parts 6b, elastic members 5 are arranged inside the base fabric 1 as described above. As the elastic member 5, a linear elastic body 5a having stretchability is used, and as the linear elastic body 5a, rubber thread is suitably used. Hereinafter, an embodiment in a case where a linear elastic body 5a is used as the elastic member 5 will be described.

As shown in FIGS. 1 and 2, the linear elastic bodies 5a are arranged such that the direction in which the linear elastic bodies 5a extend is the same direction as a longitudinal direction (x direction in FIGS. 1 and 2) of a laminated sheet 30, and a large number of linear elastic bodies 5a are arranged in parallel at predetermined intervals. That is, a large number of the linear elastic bodies 5a are arranged at intervals in a width direction (y direction in FIGS. 1 and 2) of the laminated sheet 30, and a large number of linear elastic body rows are formed. In this regard, the intervals at which the linear elastic bodies 5a are arranged in the Y direction may be substantially equal, for example, the linear elastic bodies 5a may be densely arranged at shorter intervals in a peripheral part. Further, the interval may be shortened from the central part to peripheral part of the base fabric 1. By arranging the linear elastic bodies 5a densely in the peripheral part, the side of a surface material 15 has a function as a gather when the base fabric 1 is used as the surface material 15 of an absorbent body 14. In place of this, or in combination with this, the elastic force of the linear elastic body 5a in the peripheral part and the elastic force of the linear elastic body 5a in the central part are set different from each other so that the elastic force of the linear elastic body 5a in the peripheral part is strengthened. Note that in the present embodiment, the expression "peripheral part" of the surface material 15 is referred to as around 5 to 30% in the right-side end part and around 5 to 30% in the left-side end part in the Y direction in FIG. 8 described later, and the central part of the surface material 15 is referred to as a part excluding both of the end parts.

As shown in FIG. 5, the linear elastic bodies 5a are arranged to be positioned between a first fibrous sheet 2 and a fiber material 4. In the present embodiment, one shirring part 6 extending from one end to the other end along they direction (a second direction different from the first direction) in FIGS. 1 and 2 is referred to as a "row of a shirring part". A large number of rows of the shirring parts 6 are formed at predetermined intervals in the x direction in FIGS. 1 and 2. Herein, the joined position with the linear elastic body 5a is referred to as a shirring part support point in the shirring part 6. Although the number of linear elastic bodies 5a per unit area can be arbitrarily set, by increasing the number of the linear elastic bodies 5a to reduce the interval between the linear elastic bodies 5a, the number of the shirring part support points in one row of shirring part is increased, and a protrusion part 6a and a concave part 6b in one row of shirring part 6 can be formed in a uniform shape and further the shape thereof can be maintained. According to this, the shirring part 6 does not lose the shape, and becomes preferred from the viewpoint of increasing the softness, the moisture transpiration ability, the heat dissipation, and the moisture permeability, of the base fabric 1. From such a point, the interval between the shirring parts 6, that is, the pitch interval between the protrusion parts 6a is preferably 2 mm to 7 mm. The pitch interval between the protrusion parts 6a is more preferably 3.00 mm to 6.25 mm. By narrowing the pitch interval between the protrusion parts 6a, fine shirring can be formed, so that the appearance becomes beautiful, and the contact area with the skin per one shirring becomes small, so that the touch is better, and furthermore, the surface area is increased, so that the absorbability of, for example, sweat is improved. On the other hand, by increasing the pitch interval between the protrusion parts 6a, an elastic force of rubber thread can be adequately suppressed, so that the production cost can be reduced. Note that in FIGS. 1 and 2, the shirring parts 6 are shown to be formed continuously, but may be discontinuous or shifted in the y direction depending on the number of the linear elastic bodies 5a or on the way of the arrangement of the linear elastic bodies 5a. However, in a case where shirring parts 6 are formed to be shifted in the y direction, for example, urine hardly proceeds, and the shirring parts 6 can contribute to the prevention of lateral leakage.

Herein, one example of a production method for producing a base fabric 1 by using rubber thread as the linear elastic body 5a, and using a hot-melt adhesive as the adhesive agent will be described. As described later, a paper material is preferably used as the fiber material 4, and a hydrophilic nonwoven fabric is preferably used as each of the first fibrous sheet 2 and the second fibrous sheet 3, therefore, taking as an example a case where a paper material is used as the fiber material 4, and a nonwoven fabric (for example, thermally bonded nonwoven fabric) is used as each of the first fibrous sheet 2 and the second fibrous sheet 3, a method for producing a base fabric 1 will be described. Herein, a nonwoven fabric used as the first fibrous sheet 2 is referred to as a first nonwoven fabric sheet, and a nonwoven fabric used as the second fibrous sheet 3 is referred to as a second nonwoven fabric sheet.

Firstly, a paper material as the fiber material 4 is fed out from a roll wound body. In a case where a base fabric 1 is used for an exterior of disposable pants, onto this paper material, a print layer 4a (see FIGS. 4 and 6) may be formed in advance to apply various kinds of prints. The fed-out paper material is passed through an embossing roll, and pressed between rolls to perform a mechanical softening process. This mechanical softening process may be an emboss process using a flat roll, or an emboss process using a meshing roll having a large number of protrusions on the roll surface. In a case of the latter emboss process, a large number of fine pores are opened in the paper material. When a hot-melt adhesive is intermittently sprayed onto the paper material after the emboss process, the hot-melt adhesive permeates into the fine holes, and the easiness of adhesion to the second nonwoven fabric sheet can be improved. In addition, machining other than the emboss processing may be adopted, and multiple embossing devices may be arranged to perform the emboss processing multiple times. In this case, embossing devices, which are the same ones as one another, or embossing devices, which are different from one another in the embossing direction, the emboss shape, or the size of the emboss shape, may be arranged. By performing the emboss processing, the softness of the fiber material 4 is improved, and the touch can be improved.

On the other hand, a second nonwoven fabric sheet as the second fibrous sheet 3 is fed out from a roll wound body, the second nonwoven fabric sheet, and a paper material to which a hot-melt adhesive has been applied are press bonded bypassing through flat rolls, and both of the second nonwoven fabric sheet and the paper material are laminated to produce a joined body sheet. In this joined body sheet, the second nonwoven fabric sheet and the paper material are intermittently joined.

A large number of rows of rubber threads are fed out from a roll wound body onto which a large number of rubber threads have been wound in parallel rows. The rubber threads are fed out in a pulled state with a predetermined pulling force. A hot-melt adhesive is sprayed onto the fed-out rubber threads. In this case, the adhesive agent is continuously sprayed over the entire length in the length direction of the rubber threads. Further, the adhesive agent is applied to the entire peripheral surface of the rubber threads. On the other hand, a first nonwoven fabric sheet as the first fibrous sheet 2 is fed out from a roll wound body, this first nonwoven fabric sheet is sent out so as to face the above-described joined body sheet, and rubber threads to which an adhesive agent has been applied as described above are supplied so as to be sandwiched between the joined body sheet and the first nonwoven fabric sheet. In this case, the rubber threads are supplied between a surface of the paper material of the joined body sheet and the first nonwoven fabric sheet.

The rubber threads are sandwiched between the surface of the paper material of the joined body sheet and the first nonwoven fabric sheet, and are passed through flat rolls in a sandwiched state. The joined body sheet, the rubber threads, and the first nonwoven fabric sheet are press bonded by the flat rolls, and integrally laminated. The first nonwoven fabric sheet and the paper material are joined with the rubber threads therebetween, therefore, both are intermittently joined. In this way, a laminated sheet 30 in which the second nonwoven fabric sheet and the paper material are intermittently joined, and the first nonwoven fabric sheet and the paper material are intermittently joined is produced. As needed, the laminated sheet 30 is passed through an embossing roll to perform a mechanical softening process. By performing this process, the softness of a base fabric 1 can be further improved. In this regard, as described above, in the present embodiment, the base fabric 1 is used as a surface material 15 for an absorbent body 14, therefore, the first nonwoven fabric is in contact with an absorbent body 14 that is formed of, for example, a fiber assembly made of pulp fibers, or a water-absorbing polymer. Accordingly, in place of the first nonwoven fabric sheet, a paper material that is more excellent in the liquid permeability than that of a nonwoven fabric may be used, and a two-layer structure obtained by omitting the first nonwoven fabric sheet may be used. In this case, the elastic members 5 may be arranged between the second fibrous sheet 3 and the fiber material 4. If the second fibrous sheet 3 and the fiber material 4 are joined by intermittently applying a hot-melt adhesive to the elastic members 5, the number of adhesion (joining) steps can be reduced. In addition, since the second fibrous sheet 3 comes into contact with the skin through the elastic members 5, the softness is improved as compared with a case where the second fibrous sheet 3 joined to the fiber material 4 comes into contact with the skin. Further, also in a case of arranging the elastic members 5 between the second fibrous sheet 3 and the fiber material 4, it is desired that the fiber material 4 is subjected to a mechanical softening process, and a hot-melt adhesive may be applied at least one of the second fibrous sheet 3 and the fiber material 4. In addition, as the method for intermittently applying an adhesive agent, methods for applying an adhesive agent in, for example, a linear state, a dotted state, a striped state, a spiral state, a block state, and a patterned state can be mentioned, and one of the methods may be used, or multiple methods may be used in combination.

Since the produced laminated sheet 30 has a continuous length in dimension, the laminated sheet 30 is cut into a predetermined length in the longitudinal direction (x direction in FIGS. 1 and 2) of the laminated sheet 30. In this cutting, the first nonwoven fabric sheet, the second nonwoven fabric sheet, the paper material, and the rubber threads are cut. By cutting the rubber threads, the rubber threads which have been in a pulled state are released from the pulling force, and contract due to the restoring force. Because of the contraction stress at this time, the laminated sheet 30 constituted of the first nonwoven fabric sheet, the second nonwoven fabric sheet, and the paper material receives a force in a direction in which the length of the laminated sheet 30 becomes shorter, and therefore, an uneven surface is formed in the laminated sheet 30, and shirring parts 6 are formed by the uneven surface. In this way, the base fabric 1 having a large number of shirring parts 6 is produced.

Herein, in the base fabric 1, the linear elastic bodies 5a are in a contracted state, that is, in a non-pulled state by a restoring force, a large number of shirring parts 6 extending in a direction (the width direction of the laminated sheet 30 in FIGS. 1 and 2, that is, the same direction as the y direction) perpendicular to a longitudinal direction of the linear elastic bodies 5a in this non-pulled state (the longitudinal direction of the laminated sheet 30 in FIGS. 1 and 2, that is, the same direction as the x direction) are formed, and the shirring part rows are pattern-formed on the laminated sheet 30.

By the linear elastic bodies 5a arranged inside the laminated sheet 30, elasticity is imparted to the laminated sheet 30. Therefore, when the base fabric 1 constituted of the laminated sheet 30 is pulled by a hand in the x direction in FIGS. 1 and 2, the linear elastic bodies 5a are extended, and thus the base fabric 1 is also extended and enlarged, and further, when the hand is released from this state, the linear elastic bodies 5a contract by the restoring force, and the base fabric 1 also returns to the original state in size. Since the base fabric 1 has stretchability as described above, the base fabric 1 has an excellent fit feeling to the body in a case of being used as a surface material 15 of an absorbent body 14.

In a case where a hydrophilic nonwoven fabric is used as each of the first fibrous sheet 2 and the second fibrous sheet 3, as the hydrophilic fibers, for example, from the viewpoint of the adhesiveness to a hydraulic composition, for example, vinyl alcohol-based fibers, and hydrophilic polypropylene-based fibers can be used. In addition, the basis weight of each of the first fibrous sheet 2 and the second fibrous sheet 3 is preferably 10 to 50 g/m$^2$ as an example.

In a case of using a paper material as the fiber material 4, a paper material formed of pulp paper or a material having pulp as the main raw material can be used. As the raw material pulp, for example, wood pulp, synthetic pulp, or waste paper pulp can be used. Further, the paper material 4 is not limited to natural fibers such as pulp, and regenerated fibers such as rayon can also be used. In addition, the basis weight of the fiber material 4 is preferably 10 to 50 g/m$^2$ as an example.

Figure 8:
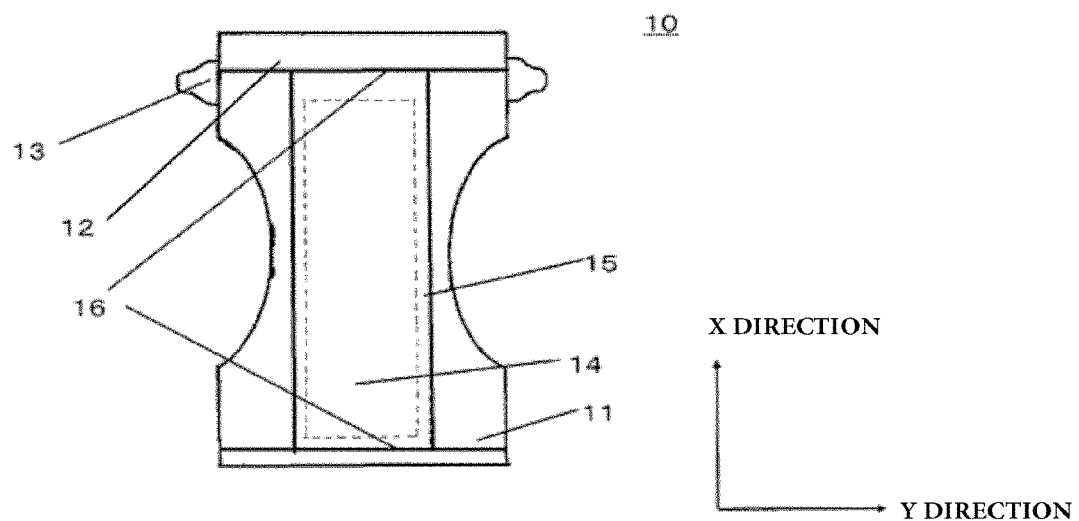
FIG. 8 is a schematic view of a disposable diaper 10 of the present embodiment.

FIG. 8 is a schematic view of a disposable diaper 10 of the present embodiment. As shown in FIG. 8, a disposable diaper 10 is constituted of, for example, an outer sheet 11 having a moisture permeable sheet, a waist part 12, a tape part 13, an absorbent body 14, and a surface material 15. The outer sheet 11, the waist part 12, and the tape part 13 are the same as those of a well-known disposable diaper, a pants-type paper diaper may be used in place of the tape part 13, and other constitutions (for example, a gather function) may also be provided. The absorbent body 14 is well known for absorbing a liquid (including a body fluid such as blood) such as sweat, and urine of a disposable diaper wearer. The absorbent body 14 is formed of, for example, a fiber assembly made of pulp fibers and the like, or a water-absorbing polymer, and is joined to an outer sheet 11 by, for example, a hot-melt adhesive, or ultrasonic joining in a state of being accommodated in, for example, a bag-shaped fiber material. In addition, a surface material 15 may be joined to the outer sheet 11 after the absorbent body 14 is joined to the surface material 15 instead of the outer sheet 11. In this case, if the surface material 15 is joined to the outer sheet 11 so as to be detachably attached to the outer sheet 11 by, for example, a tape, the outer sheet 11 can be used multiple times by exchanging the absorbent body 14 and the surface material 15. In particular, in a case where the base fabric 1 described above is adopted at least in a part of the outer sheet 11 as disposable pants, since the base fabric 1 can withstand multiple times of washing, the outer sheet 11 can be repeatedly used. Further, the absorbent body 14 absorbs excrement, and therefore, it is desired to add a deodorizer to the absorbent body 14. As the deodorizer, activated carbon, zeolite, silica, ceramic, Oya tuff stone, charcoal polymer, carbon nanotube, carbon nanohorn, an organic acid such as citric acid, and succinic acid, or alum (potassium alum) can be used. In the present embodiment, alum is added to at least one of the fiber assembly and the bag-shaped fiber material. In addition to this, or in place of this, a deodorizer such as alum may be added to a part excluding a second fibrous sheet 3, which is arranged on the surface side for applying to the skin of the surface material 15. This is because as the deodorizing liquid, a liquid in which a metal has been dissolved is sometimes used.

In addition, in a state that a surface material 15 is placed on an outer sheet 11, the lower end part of the outer sheet 11 and the waist part 12 of the outer sheet 11 are folded so as to wrap around both ends in the X direction of the surface material 15, and then the surface material 15 may be joined to the outer sheet 11 in joining parts 16. Further, although not shown in the drawing for the sake of simplicity, joining in the Y direction may be performed in a similar manner. The joining of the outer sheet 11 and the surface material 15 may be direct joining or indirect joining. As the indirect joining, for example, the joining may be performed with an absorbent body 14 interposed between the outer sheet 11 and the surface material 15. In this case, the outer sheet 11, the absorbent body 14, and the surface material 15 may be joined by pressure joining, press-cut joining, or contact-cut joining. Further, the outer sheet 11 and the surface material 15 may be indirectly joined with a member arranged therebetween instead of the absorbent body 14.

In addition, in FIG. 8, the length of the surface material 15 is shorter than the length of the outer sheet 11 in both of the X and Y directions, but the surface material 15 may be made longer than the outer sheet 11 in length in each of the X and Y directions so as to wrap around the outer sheet 11 by folding the end parts of the surface material 15. In this case, for example, a double-sided tape, or a hook and loop fastener may be arranged on the end parts of the surface material 15 to join the outer sheet 11, or the joining may be performed by hot melt joining, ultrasonic joining, or heat seal joining. In addition, without folding the end part of the surface material 15, the outer sheet 11 and the surface material 15 may be joined to each other by applying a pressure-sensitive adhesive such as a double-sided tape or arranging mechanical engagement in an end part or the vicinity of the end part of the surface material 15.

The surface material 15 is constituted of the base fabric 1 described above, and the second fibrous sheet 3 comes into contact with the skin of a wearer. That is, in the present embodiment, the surface material 15 is joined to the outer sheet 11, so that the first fibrous sheet 2 is positioned on the side of the absorbent body 14.

The way of joining the surface material 15 as described above can also be applied to the disposable pants 20 described later or to other disposable articles.

Note that the disposable diaper 10 in FIG. 8 shows merely an outline, and for example, the dimension is not strict (the same applies also to the other drawings).

Figure 9:
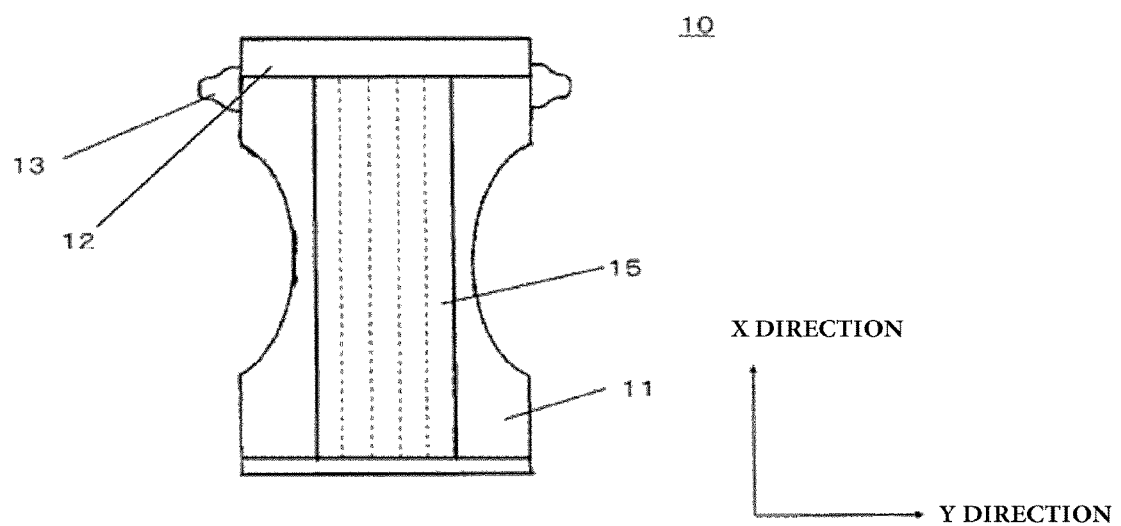
FIG. 9 is a diagram showing a disposable diaper 10 provided with elastic members on an outer sheet along the X direction.

FIG. 9 is a diagram showing a disposable diaper 10 provided with elastic members 5 on an outer sheet 11 along the X direction. As described above, if the longitudinal direction (X direction) of the outer sheet 11 and the longitudinal direction of the base fabric 1 are matched with each other, the conveying direction of the base fabric 1 and the conveying direction of the outer sheet 11 are matched with each other in the production process, and thus, for example, a step of inverting the base fabric 1 by 90 degrees is not required, and the disposable diaper 10 can be produced cheaply. In a case where a disposable diaper 10 is used, the second fibrous sheet 3 (for example, hydrophilic nonwoven fabric) having softness comes into contact with the skin, and further the surface material 15 fits the crotch by the elastic force of the elastic members 5, and therefore, the disposable diaper 10 is comfortable to wear. Further, since the contact area with the user is reduced by shirring parts 6, the touch becomes better. In addition, even in a case where urine is discharged, the fiber material 4 that has more excellent liquid permeability than the second fibrous sheet 3 has rapidly leads the urine to the absorbent body 14, and therefore, the surface material 15 is kept dry due to the ventilation in the space 9 shown in FIGS. 6 and 15, and there is no stuffiness. Further, the surface area of each of the second fibrous sheet 3 and the fiber material 4 is larger than the surface area in a case where the elastic members 5 have not been provided, by the shirring parts 6 formed by the expansion and contraction of the elastic members 5, and even when the amount of urine is large, the urine can be rapidly led to the absorbent body 14. Moreover, the elastic force of the elastic members 5 is not lost, and therefore, the fit feeling and the wearing comfort do not deteriorate.

Figure 10:
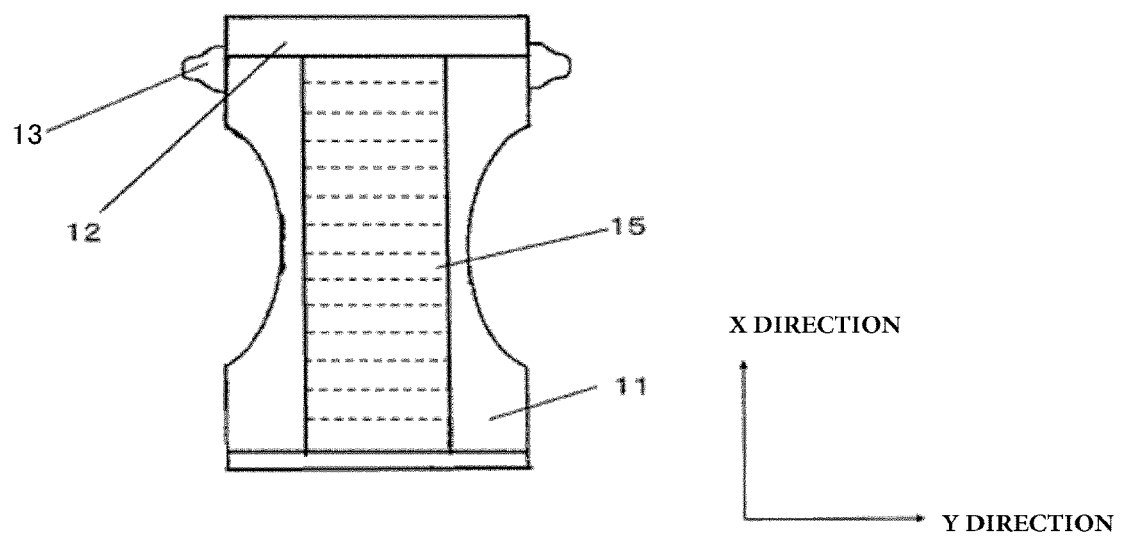
FIG. 10 is a diagram showing a disposable diaper 10 provided with elastic members on an outer sheet along the Y direction.

FIG. 10 is a diagram showing a disposable diaper 10 provided with elastic members 5 on an outer sheet 11 along the Y direction. Although omitted in FIG. 10, as is apparent from FIGS. 2 and 3, the shirring parts 6 are formed along the X direction in a case where the elastic members 5 are arranged on the outer sheet 11 along the Y direction. By the multiple shirring parts 6 formed along the X direction, the flowing of urine in the Y direction can be prevented, and the lateral leakage can be prevented.

Figure 15:
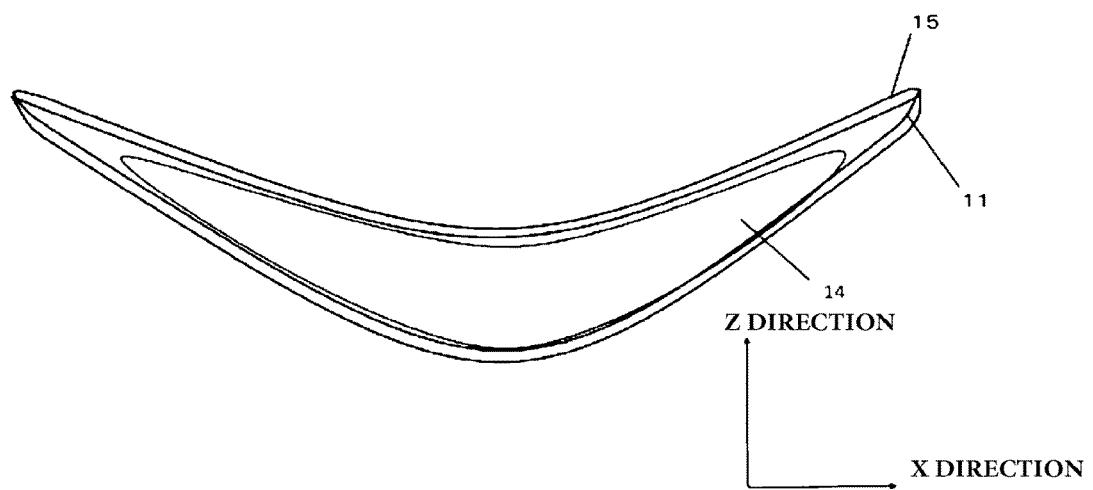
FIG. 15 is a sectional view of a disposable diaper 10 along the X direction.
Figure 17:
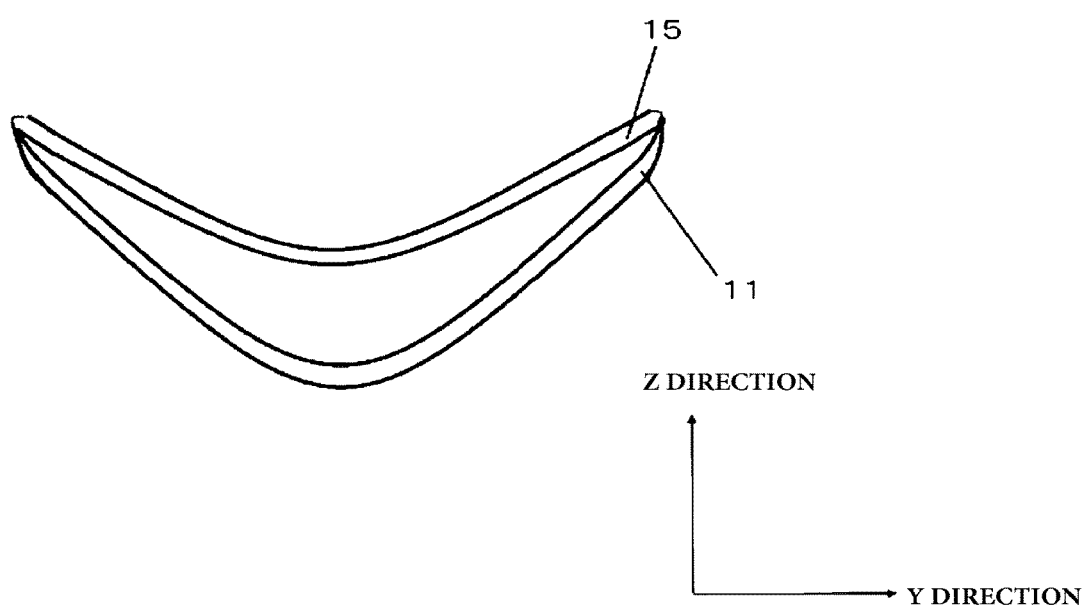
FIG. 17 is a sectional view of a disposable diaper 10 along the Y direction.

As is apparent from FIGS. 9 and 10, the elastic members 5 are arranged on the entire surface including the central part of the surface member 15 of the present embodiment, and therefore, the elastic force of the elastic members 5 acts on the part that is in contact with the crotch of the user, and the surface material 15 fits the user. FIG. 15 is a sectional view of a disposable diaper 10 along the X direction, and as is apparent from FIG. 15, the disposable diaper 10 is curved in a V shape by multiple elastic members 5. As described above, both ends in the X direction (longitudinal direction) of the disposable diaper 10 are lifted in the Z direction (third direction), and therefore, when the disposable diaper 10 is worn by a user, the disposable diaper 10 fits to the lower part of the body of the user. FIG. 17 is a sectional view of a disposable diaper 10 along the Y direction, and as is apparent from FIG. 17, the disposable diaper 10 is curved in a V shape by multiple elastic members 5. As described above, both ends in the Y direction (short direction) of the disposable diaper 10 are lifted in the Z direction, and therefore, the lateral leakage of, for example, urine can be prevented. In particular, in a case where the surface material 15 is applied to a sanitary napkin in place of the disposable diaper 10, the lateral leakage of menstrual blood can be prevented without increasing the size of the sanitary napkin. In this way, in order to prevent the lateral leakage from a disposable diaper 10 or a sanitary napkin, as described above, it is only necessary to densely arrange multiple elastic members 5 or to increase the elastic force in the peripheral part as compared in the central part. In addition, in accordance with a general body shape of an adult male, an adult female, or a child (male or female), by appropriately selecting the elastic force of elastic members 5 and the arrangement (density) of elastic members 5 so as to fit the body, a disposable product may be sterically designed and produced.

Figure 11:
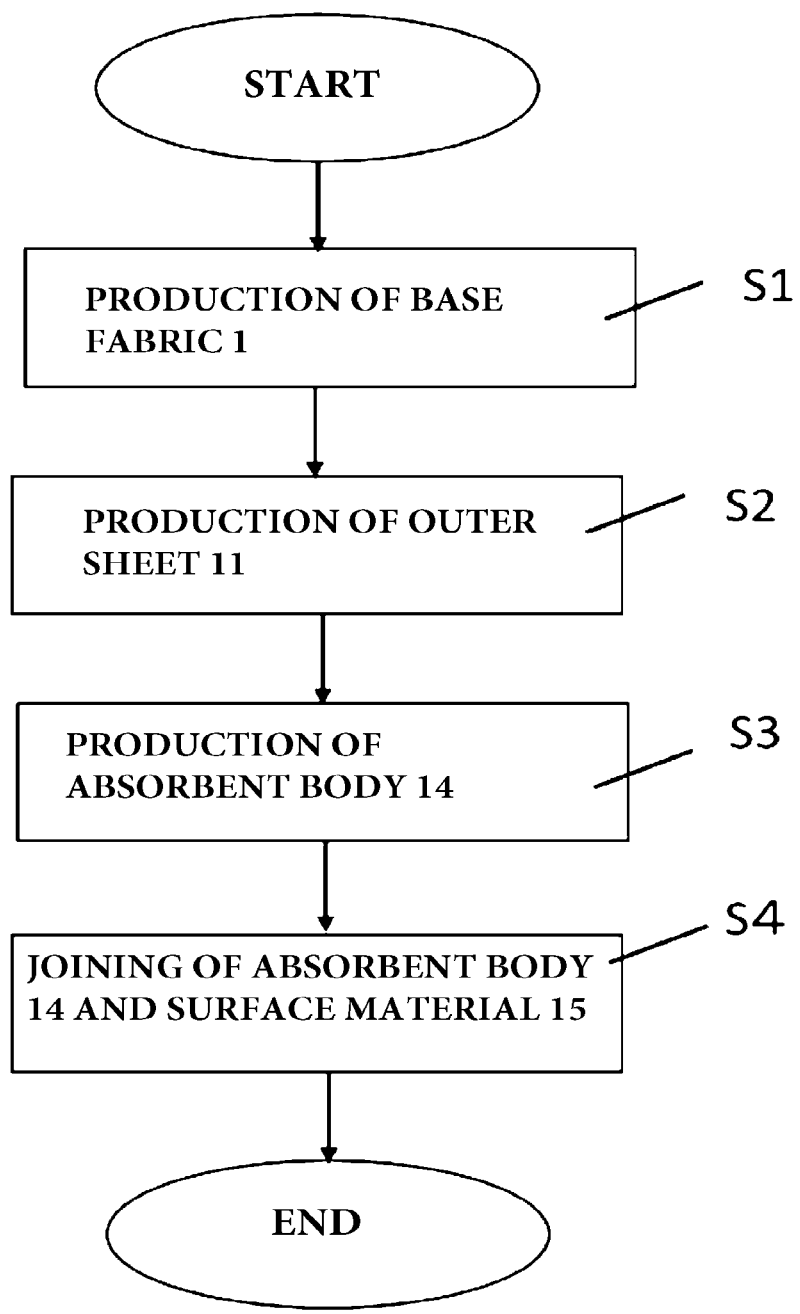
FIG. 11 is a flowchart showing a method for producing a disposable diaper 10 of the present embodiment.

FIG. 11 is a flowchart showing a method for producing a disposable diaper 10 of the present embodiment. The production of the disposable diaper 10 is conducted under the control of a control device (not shown) equipped with a CPU in a factory automation (FA) factory. In step S1, a base fabric 1 is produced as described above.

In step S2, an outer sheet 11 is produced by a well-known method.

In step S3, an absorbent body 14 is produced from, for example, a fiber assembly made of pulp fibers, or a water-absorbing polymer.

Note that the order of from step S1 to step S3 may be changed.

In step S4, joining of the absorbent body 14 and the surface material 15 is performed. As described above, in this joining, a surface material 15 may be joined to an outer sheet 11 after the absorbent body 14 is joined to the outer sheet 11, or the absorbent body 14 and the surface material 15, which have been joined to each other, may be joined to the outer sheet 11. In this case, the absorbent body 14 and the surface material 15, which have been joined to each other, may be attached to the surface material 15 so as to be detachable.

Figure 12:
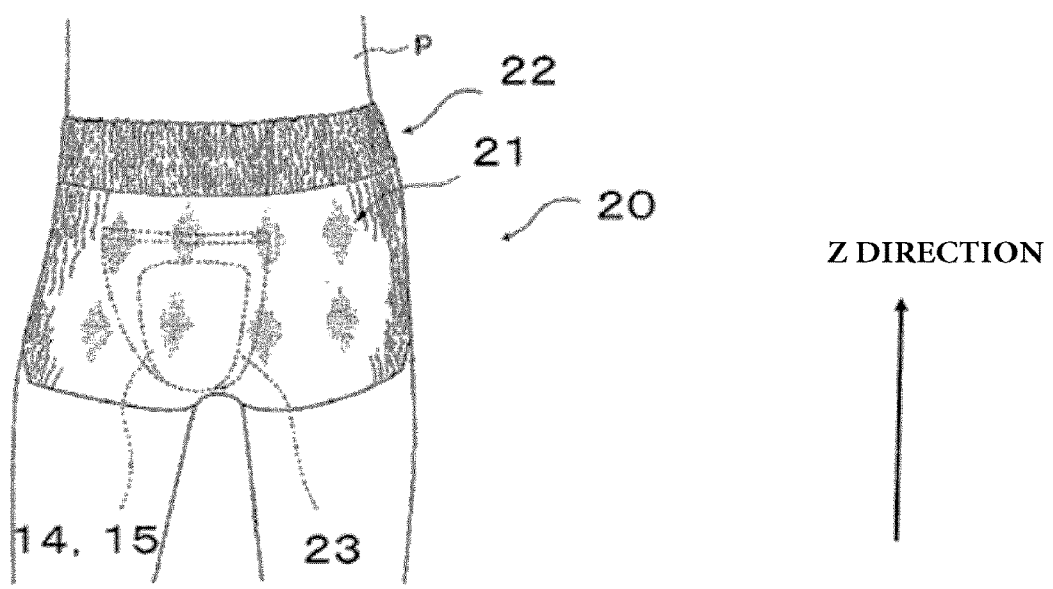
FIG. 12 is a schematic view of disposable pants 20 of the present embodiment.

The absorbent body 14 and the surface material 15, which have been described above, can be applied also to disposable pants. FIG. 12 is a schematic view of disposable pants 20 of the present embodiment. The disposable pants 20 cover the entire body part of a user P, and have a body part applying part 21 including a part for lightly pressing the lower abdomen, and a lumbar part applying part 22 that has been arranged on the upper side of the body part applying part 21, includes an elastic member, for example, rubber, and is put around the waist of the user P. As the base fabric of at least one of the body part applying part 21 and the lumbar part applying part 22, the above-described base fabric 1 may be applied, and a layer may be additionally applied to the base fabric 1.

In addition, in the disposable pants 20, an elastic sheet 23 is stretched between the front part and the rear part of the body part applying part 21 on the inner side (the side in contact with the body) of the body part applying part 21, and on the inner side (the side in contact with the skin of a user P) of the elastic sheet 23, the absorbent body 14 and the surface material 15, which have been described above, are attached. Further, the surface material 15 has elasticity, therefore, the elastic sheet 23 is omitted, and the absorbent body 14 and the surface member 15 may be directly attached onto the inner side of the body part applying part 21 so as to be exchangeable.

The disposable pants 20 shown in FIG. 12 has a function as a diaper as described above, and can be used as a diaper for an adult or also as a diaper for an infant.

Further, the constitution of the surface material 15 has been described as a two-layer structure in which elastic members 5 are arranged between a second fibrous sheet 3 and a fiber material 4, but in a case where a bag-shaped fiber material is used as the absorbent body 14 as described above, the fiber material 4 is omitted, and a fiber layer may be used by utilizing the liquid diffusibility of a fiber material for the absorbent body 14.

MEASUREMENT EXAMPLE

Hereinafter, the description of measurement examples of a disposable base fabric will be continued.

Measurement Example 1

A hydrophilic nonwoven fabric was used as a permeable sheet, paper of 100% pulp (paper sheet for toilet paper) was used as a fiber sheet, and urethane rubber having a diameter of 620 dtex was used as an elastic member. A hot-melt adhesive was applied to the urethane rubber, and the hydrophilic nonwoven fabric and the paper of 100% pulp were intermittently joined with the urethane rubber therebetween to prepare a test piece.

Comparative Measurement Example 1

A hydrophilic nonwoven fabric constituting a surface of an absorbent body of a disposable diaper was collected, and this nonwoven fabric was used as a disposable base fabric as a permeable sheet. In this regard, this test piece does not have a fiber sheet or an elastic member.

Comparative Measurement Example 2

A hydrophilic nonwoven fabric constituting a surface of an absorbent body of a disposable diaper was collected, and this nonwoven fabric was used as a disposable base fabric as a permeable sheet. In this regard, this test piece does not have a fiber sheet or an elastic member.

Comparative Measurement Example 3

A hydrophilic nonwoven fabric constituting a surface of an absorbent body of a disposable diaper was collected, and this nonwoven fabric was used as a disposable base fabric as a permeable sheet. In this regard, this test piece does not have a fiber sheet or an elastic member.

Comparative Measurement Example 4

A hydrophilic nonwoven fabric constituting a surface of an absorbent body of a disposable diaper was collected, and this nonwoven fabric was used as a disposable base fabric as a permeable sheet. In this regard, this test piece does not have a fiber sheet or an elastic member.

Comparative Measurement Example 5

A hydrophilic nonwoven fabric constituting a surface of an absorbent body of a disposable diaper was collected, and this nonwoven fabric was used as a disposable base fabric as a permeable sheet. In this regard, this test piece does not have a fiber sheet or an elastic member.

At first, the moisture absorption and quick drying ability (transpiration ability) and the moisture permeability of each of disposable base fabrics of Measurement Example 1 and Comparative Measurement Examples 1 to 5 were evaluated.

Firstly, as for the moisture absorption and quick drying ability (transpiration ability), both of the moisture absorption ability and the quick drying ability were evaluated comprehensively by performing a transpiration (II) test (Boken standard BQE A 028).

A test piece having a diameter of around 9 cm was prepared for each of the disposable base fabrics of Measurement Example 1 and Comparative Measurement Examples 1 to 5, and a mass (W) of each of the test pieces and a petri dish was measured. Next, 0.1 mL of water was added dropwise in the petri dish, the test piece was placed on the water, and a mass (W0) was measured. The petri dish was left to stand under standard conditions (20° C., and humidity of 65% RH), and a mass (Wt) was measured after the lapse of each of the predetermined times (5 minutes, 10 minutes, and then every 10 minutes up to 60 minutes). A transpiration rate (%) for each of the predetermined times was calculated from the measured masses of W, W0, and Wt by using the following equation (1).

$$\text{Transpiration rate (\%)} = \{(W0-Wt)/(W0-W)\} \times 100 \quad (1)$$

The results are shown in Table 1.

TABLE 1

| | Transpiration rate (%) | | | | | | |
|---|---|---|---|---|---|---|---|
| | 5 minutes | 10 minutes | 20 minutes | 30 minutes | 40 minutes | 50 minutes | 60 minutes |
| Measurement Example 1 | 8.1 | 20.3 | 46.7 | 70.4 | 86.4 | 94.2 | 96.1 |
| Comparative Example 1 | 2.5 | 6.2 | 12.1 | 18.0 | 23.9 | 29.9 | 35.5 |
| Comparative Example 2 | 0.7 | 2.6 | 5.1 | 8.3 | 11.2 | 16.6 | 22.7 |
| Comparative Example 3 | 1.5 | 2.7 | 6.0 | 9.9 | 12.0 | 15.7 | 18.2 |
| Comparative Example 4 | 2.9 | 4.2 | 8.5 | 11.7 | 17.9 | 21.1 | 25.6 |
| Comparative Example 5 | 2.8 | 6.4 | 12.4 | 18.2 | 23.6 | 29.9 | 38.1 |

As is apparent from the results of transpiration rate shown in Table 1, it can be understood that in Comparative Measurement Examples 2 to 4, all of the transpiration rates were 30% or less even after the lapse of 60 minutes, and in Comparative Measurement Examples 1 and 5, both of the transpiration rates were less than 15% after the lapse of 20 minutes and 40% or less even after the lapse of 60 minutes. On the contrary, it can be understood that in Measurement Example 1, the transpiration rate exceeded 20% after the lapse of 10 minutes, the transpiration rate exceeded 40% after the lapse of 20 minutes, after that, the transpiration rate exceeded 70% after the lapse of 30 minutes, the transpiration rate exceeded 85% after the lapse of 40 minutes, the transpiration rate exceeded 90% after the lapse of 50 minutes, and the transpiration rate exceeded 95% after the lapse of 60 minutes.

In addition, in Boken standard BQE A 028, it is said that as a measure of evaluation, the transpiration rate in 20 minutes after the start of the test is preferably 50% or more for a woven fabric and 40% or more for a knit in a case of being used for the application for sport, and is preferably 40% or more for a woven fabric and 30% or more for a knit in a case of being used for the general application.

Accordingly, it can be said that the surface material 15 of Measurement Example 1 was able to obtain a transpiration rate of 45% or more, and therefore, can be worn comfortably for the application for sport, or also for the general application.

From the above, it can be understood that a disposable article obtained by joining the surface material 15 of Measurement Example 1 with a disposable base fabric has extremely high moisture absorption and quick drying ability (transpiration ability).

Next, the moisture permeability (g/m$^2$·h) was determined by performing an A-1 method (calcium chloride method) of JIS L 1099 (2012), and the moisture permeability was evaluated.

Note that the moisture permeability is defined as a value obtained by converting the mass (g) of the water vapor permeating a textile product per 1 m$^2$×1 hour of the textile product at a prescribed temperature and humidity.

A test piece was taken from each of the disposable base fabrics of Measurement Example 1 and Comparative Measurement Examples 1 to 5 in accordance with 6.3 (cloth-like sample and the test piece thereof) of JIS L 0105.

A device and a material, for example, a moisture-permeable cup, a thermo-hygrostat, a round plate, and a moisture absorbent, which are prescribed in the calcium chloride method, were prepared, and the experiment was performed.

At first, around 33 g of the moisture absorbent was placed in the moisture-permeable cup that had been warmed up to around 40° C., the moisture-permeable cup was vibrated to uniformly prepare the moisture absorbent, then the surface was flattened and smoothed with a spatula, and the distance between the moisture absorbent and the lower surface of the test piece was adjusted to be 3 mm using the round plate.

Next, for the disposable base fabrics of Measurement Example 1 and Comparative Measurement Examples 1 to 5, three test pieces each having a diameter of around 90 mm were sampled in accordance with 6.3 (cloth-like sample and the test piece thereof) of JIS L 0105.

Each test piece was placed so as to be concentric with the moisture-permeable cup and such that the surface of the test piece faces the moisture absorbent, a packing and a ring were successively mounted and fixed with a wing nut, and then a mounting-side surface was sealed with a vinyl adhesive tape to prepare a test specimen. The test specimen was placed at a position where the wind speed around 10 mm above the test piece does not exceed 0.8 m/s in a thermo-hygrostat at a temperature of 40° C.±2° C. and a humidity of (90±5)% RH. The test specimen was taken out after 1 hour, and a mass (a1) was immediately measured with an accuracy of up to 1 mg. After the measurement, the test specimen was again placed at the same position in the thermo-hygrostat, the test specimen was taken out after 1 hour, and a mass (a2) was immediately measured with an accuracy of up to 1 mg. From the measured masses a1 and a2, the moisture permeability PA1 (g/m$^2$·h) was calculated using the following equation (2).

$$\text{Moisture permeability } PA1 \ (g/m^2 \cdot h) = (a2-a1)/SA1 \quad (2)$$

In the equation (2), the a2−a1 is an amount of change of the mass per hour (g/h) of the test specimen, and the SA1 is a moisture permeation area (m$^2$).

Each of the test results was rounded to an integer in accordance with the rule of average of 3 times of JIS Z 8401 (rounding method). The obtained results are shown in Table 2.

TABLE 2

| | Moisture permeability (g/m$^2$ · h) |
|---|---|
| Measurement Example 1 | 521 |
| Comparative Example 1 | 766 |
| Comparative Example 2 | 737 |
| Comparative Example 3 | 400 |
| Comparative Example 4 | 575 |
| Comparative Example 5 | 548 |

As is apparent from the results of moisture permeability shown in Table 2, in Comparative Measurement Examples 3, 4, and 5, all of the moisture permeabilities were 600 g/m$^2$·h or less, and in Measurement Example 1, the moisture permeability was 521 g/m$^2$·h in spite of having a multilayer structure. It can be understood that the moisture permeability in Measurement Example 1 is not inferior to those of Comparative Measurement Examples 3, 4, and 5.

From the above, it can be understood that a disposable article obtained by joining the surface material 15 of Measurement Example 1 with a disposable base fabric has favorable moisture permeability.

Next, with regard to Measurement Example 1 and Comparative Measurement Examples 1 to 5, the evaluation results of moisture permeability, and the evaluation results of transpiration ability after 20 minutes and 60 minutes are shown in Table 3.

As is apparent from the evaluation results of moisture permeability and the evaluation results of transpiration ability shown in Table 3, the surface material 15 of Measurement Example 1 has higher transpiration rate as compared with those of functional base fabric materials of Comparative Measurement Examples 1 to 5, and is not inferior to those of functional base fabric materials of Comparative Measurement Examples 1 to 5 even in the moisture permeability in spite of having a multilayer structure. Accordingly, a disposable article obtained by joining the surface material 15 of Measurement Example 1 with a disposable base fabric has a high transpiration rate, therefore, is favorable in wearing comfort.

TABLE 3

| | Moisture permeability (g/m² · h) | Transpiration rate (%) after 20 minutes | Transpiration rate (%) after 60 minutes |
|---|---|---|---|
| Measurement Example 1 | 521 | 46.7 | 96.1 |
| Comparative Example 1 | 766 | 12.1 | 35.5 |
| Comparative Example 2 | 737 | 5.1 | 22.7 |
| Comparative Example 3 | 400 | 6.0 | 18.2 |
| Comparative Example 4 | 575 | 8.5 | 25.6 |
| Comparative Example 5 | 548 | 12.4 | 38.1 |

Next, the description of the second embodiment will be continued. In the second embodiment, the elastic force of the elastic members 5 is effectively utilized, and the description will be continued below with reference to the drawings. Note that the same reference signs are given to the same members as those in the above-described embodiment, and the description thereof will be omitted.

Figure 13:
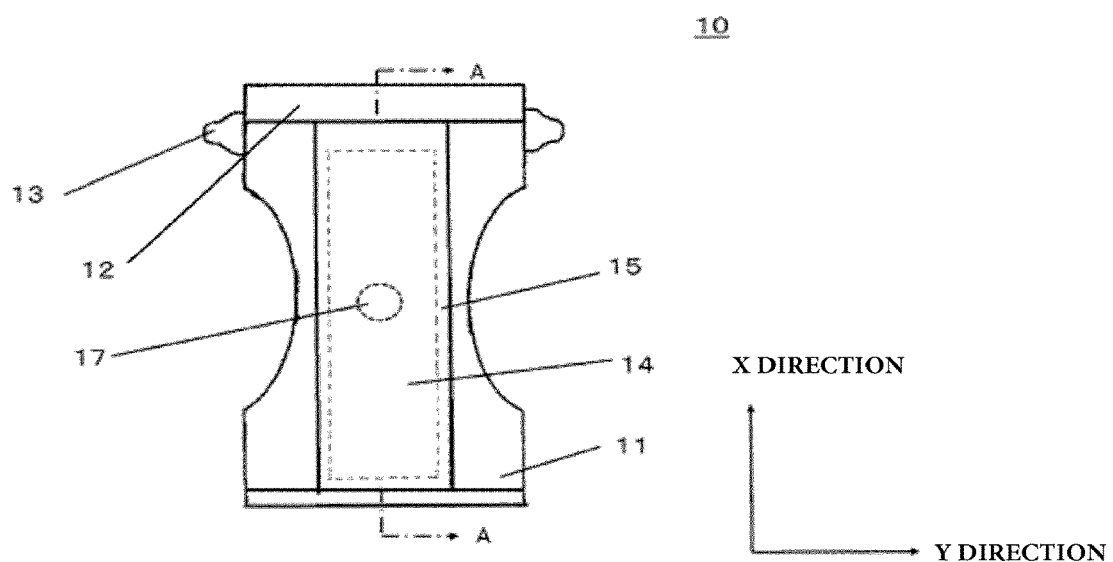
FIG. 13 is a schematic view of a disposable diaper 10 of the second embodiment.
Figure 14:
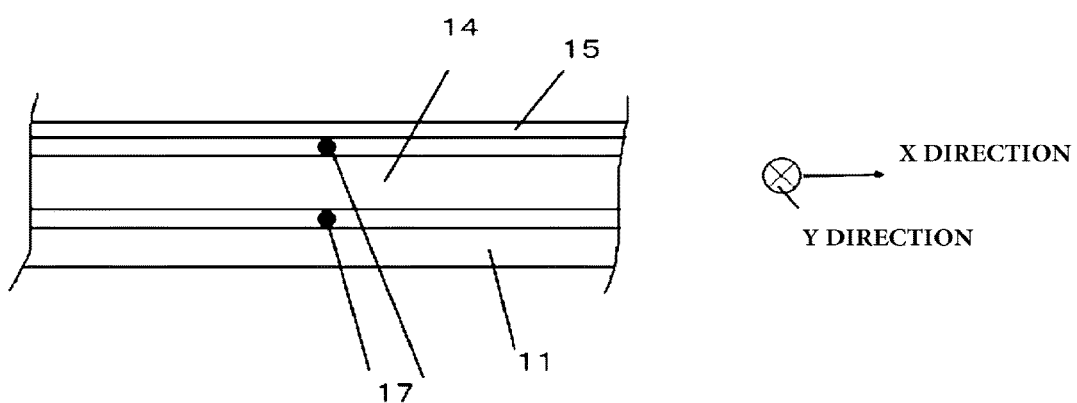
FIG. 14 is a sectional view along the line A-A of FIG. 13.

FIG. 13 is a schematic view of a disposable diaper 10 of the second embodiment, and FIG. 14 is a sectional view along the line A-A of FIG. 13. In the present second embodiment, the elastic force of the elastic members 5 is not hindered by the joining of the absorbent body 14. For example, in a case where the absorbent body 14 is accommodated in a bag-shaped fiber material, and is joined to the surface material 15 in an accommodated state, since there is no elasticity in this bag-shaped fiber material, the elastic members 5 may not expand or contract even if both ends of the surface material 15 are pulled in the X direction. In particular, as the thickness of the absorbent body 14 increases, the elastic members 5 become difficult to expand and contract. In the present second embodiment, as shown in FIGS. 13 and 14, for example, a hot-melt adhesive 17 is applied onto both surfaces in the vicinity of the center of the absorbent body 14 to join with the surface material 15 and the outer sheet 11. By performing such a joining, in a case where both ends of the surface material 15 are pulled in the X direction, the surface material 15 extends in the X direction due to the elasticity of the elastic members 5, and the fit feeling of the surface material 15 is further improved. In particular, in a case of applying the joining described above to the disposable pants 20 shown in FIG. 12, when a user P wears the disposable pants 20, an elastic force acts in the Z direction of FIG. 12, and therefore, the disposable pants 20 are not displaced downward in the Z direction due to the weight of excrement. In this regard, the joining point of the absorbent body 14 is not limited to the central part, but may be either one of both ends, or may be one side (for example, on the side of the surface member 15) of the absorbent body 14. Further, the absorbent body 14 may only be placed in a space formed by joining the surface material 15 and the outer sheet 11 without joining with the bag-shaped fiber material. In this case, a bag-shaped fiber material is omitted, and a fiber assembly made of, for example, pulp fibers, or a water-absorbing polymer is formed in this space, and the formed fiber assembly or water-absorbing polymer may be placed on the outer sheet 11.

Figure 16:
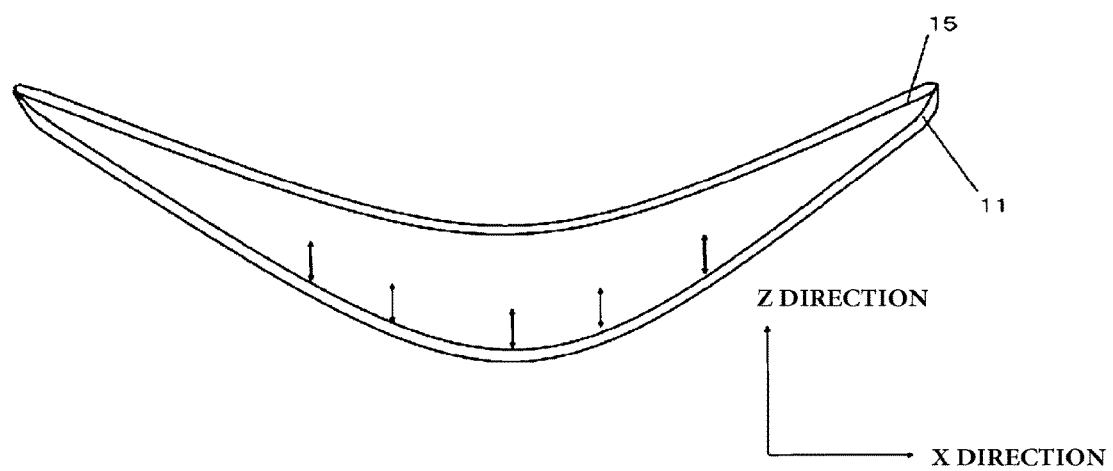
FIG. 16 is a diagram showing a direction in which elasticity acts when an elastic member is joined to an exterior sheet 11.

In addition, the surface material 15 is not also limited to the base fabric 1, and may be the one obtained by joining a permeable sheet to elastic members 5, or the one obtained by joining a fiber material to elastic members 5, or the elastic members 5 may be omitted as long as the base fabric itself has elasticity. Further, the elastic members 5 may be joined to the outer sheet 11 having a moisture permeable sheet, and a film material having elasticity may be used as the outer sheet 11. As shown in FIG. 15, in a case where an absorbent body 14 absorbed excrement, the absorbent body 14 and the outer sheet 11 having a moisture permeable sheet or a permeable film are brought into close contact with each other due to the weight of the excrement, and the steam may be trapped inside the outer sheet 11. However, in a case where the elastic member 5 was joined to the outer sheet 11, as shown in FIG. 16, an elastic force acts in the Z direction, a space (gap) can be formed between the outer sheet 11 and the absorbent body 14, the steam is transferred from the space to the outside of the outer sheet 11, and there is no stuffiness inside of the outer sheet 11. Further, in a case where the elastic member 5 was joined to the outer sheet 11, the surface area is increased as compared with that in a case where the elastic member 5 was not joined, therefore, urine and sweat are easily vaporized, and the use feeling of a disposable diaper 10 and disposable pants 20 is improved. In this regard, in a case where the elastic member 5 was joined to the outer sheet 11, the elastic member 5 on the side of the surface member 15 may be omitted. Further, in a case where a bag-shaped fiber material was used as the absorbent body 14 as described above, the fiber material 4 on the side of the surface member 15 may be omitted. In addition, in FIG. 16, in order to simplify the drawing, illustration of the absorbent body 14 is omitted.

The present embodiment has been described above, but is not limited thereto, and it goes without saying that various changes and appropriate combinations may be made. For example, as for the arrangement aspect of the linear elastic bodies 5a, it is not limited to an aspect of linear elastic bodies 5a linearly extending in the X direction, and may be an aspect of linear elastic bodies 5a arranged intermittently, may be an aspect of curving curved linear elastic bodies 5a arranged in parallel, or may be an aspect of wavy curved linear elastic bodies 5a arranged side by side irregularly. In the arrangement of a large number of linear elastic bodies 5a, each of the linear elastic bodies 5a may be a combination of linear elastic bodies 5a each having different expansion and contraction rate. The elastic member 5 is not limited to the linear form, and an elastic body in a sheet shape, in which a large number of holes or cuts are provided so as to have a predetermined permeability, may also be used.

Moreover, the disposable article can also be applied to a disposable article for an animal without being limited to a disposable article for a human.

In addition, the surface material 15 of the present embodiment may be combined with, for example, a sanitary napkin, or an armpit sweat-removing pad of underwear or clothes. Further, the base fabric 1 may be sold in combination with, for example, ordinary underwear, a brassiere, or a hat/cap. In this case, the base fabric 1 may be made into a sheet so as to fit a crotch part of underwear, and sold as a set of multiple sheets, the base fabric 1 may be made so as to be processed (cut out with scissors) by a user, or the base fabric 1 may be made so as to have perforations for cutting out.

Of course, the absorbent body 14 and the surface material 15 may be sold as a set, or may be sold in combination with the products described above. In this case, the sale may be conducted at actual stores or in internet shopping sites. In a case of selling in the internet shopping sites, when a disposable item is purchased, sale of the surface material 15 may be promoted. In this case, a user can input a size of the surface material 15 (for example, 10 sheets of 10 cm×10 cm), or a possible size and the number of possible sheets may be displayed on the web screen so as to be selected by a user.

REFERENCE SIGNS LIST

1: Base fabric, 2: first fibrous sheet, 3: second fibrous sheet, 4: fiber material, 5: elastic member, 6: shirring part, 10: disposable diaper, 14: absorbent body, 15: surface material, and 20: disposable pants.

The invention claimed is:

1. A disposable article, comprising:
an air permeable sheet having air permeability;
a fiber sheet having liquid diffusibility; and
an elastic member located between the air permeable sheet and the fiber sheet,
wherein the air permeable sheet, the fiber sheet, and the elastic member are joined by applying an adhesive to a surface of the elastic member and then attaching the air permeable sheet and the fiber sheet to the elastic member while the elastic member is in a stretched state, and
a transpiration rate of the disposal article determined by the equation:

Transpiration rate (%)=$\{(W0-Wt)/(W0-Wt)\}\times100$, exceeds 40%, where

W is a weight of a test piece of the disposal article and a petri dish under a standard condition of 20° C. and 65% RH, W0 is a weight of the test piece and the petri dish to which 0.1 mL of water is added, and Wt is a weight of the test piece and the petri dish measured after the 0.1 mL of water is added and left in the standard condition for 20 minutes.

2. The disposable article of claim 1, wherein the transpiration rate of the disposal article exceeds 95% when Wt in the equation is a weight of the test piece and the petri dish measured after the 0.1 mL of water is added and left in the standard condition for 60 minutes.

3. The disposal article of claim 1, wherein the air permeable sheet and the fiber sheet are joined via the elastic member such that a space is formed between the air permeable sheet and the fiber sheet.

4. The disposal article of claim 1, wherein the fiber sheet is subjected to a mechanical softening process prior to be joined with the air permeable sheet and the elastic member.

5. The disposal article of claim 1, wherein the fiber sheet is a paper material comprising pulp and has a basis weight of 10 to 50 g/m$^2$.

6. The disposal article of claim 1, wherein the fiber sheet comprises a deodorant.

7. The disposal article of claim 1, wherein
the elastic member is a plurality of linear elastic members, and
the disposal article has a plurality of shirring portions formed by elastic forces of the plurality of linear elastic members.

8. The disposal article of claim 7, wherein the plurality of linear elastic members is provided such that the plurality of shirring portions is discontinuously formed.

9. The disposal article of claim 7, wherein the shining portions form gathers by the elastic forces of the plurality of linear elastic members.

* * * * *